United States Patent [19]

Inglima

[11] Patent Number: 5,109,218
[45] Date of Patent: Apr. 28, 1992

[54] HYDROCARBON DETECTION CIRCUIT

[75] Inventor: Salvatore M. Inglima, Chester, N.Y.

[73] Assignee: Leak-X Corporation, Bronx, N.Y.

[21] Appl. No.: 561,842

[22] Filed: Aug. 2, 1990

[51] Int. Cl.⁵ .............................................. G08B 21/00
[52] U.S. Cl. .................................... 340/605; 340/604; 340/620; 73/304 R; 200/61.05
[58] Field of Search ............... 340/604, 605, 620, 618; 73/304 R, 49.2 T; 200/61.04, 61.05

[56] References Cited

U.S. PATENT DOCUMENTS

| | | | |
|---|---|---|---|
| 4,660,026 | 4/1987 | Chandler | 340/605 X |
| 4,926,129 | 5/1990 | Wasley et al. | 340/605 X |
| 4,931,775 | 6/1990 | Sheriff | 200/61.05 X |

FOREIGN PATENT DOCUMENTS

| | | |
|---|---|---|
| 2601410 | 7/1977 | Fed. Rep. of Germany . |
| 2837920 | 3/1980 | Fed. Rep. of Germany . |
| 52-17891 | 6/1975 | Japan . |

Primary Examiner—Jin F. Ng
Assistant Examiner—Jeffery A. Hofsass
Attorney, Agent, or Firm—Sprung Horn Kramer & Woods

[57] ABSTRACT

A circuit for detecting hydrocarbons comprises an input circuit receptive of an input signal representative of the electron movement in an unknown sample to be detected for producing a first amplified signal and a signal processing circuit receptive of the first amplified signal from the input circuit for producing a first output signal when the input signal represents the presence of hydrocarbons. The input circuit comprises four transistors connected as common base amplifiers with the base of a first of the four transistors receptive of the input signal, the base of a second of the four transistors connected to the emitter of the first transistor, the base of a third of the four transistors connected to the emitter of the second transistor, the base of a fourth of the four transistors connected to the emitter of the third transistor to produce the first amplified signal at the collector of the fourth transistor and wherein for the first transistor $70 < hfe \leq 120$, for the second transistor $150 \leq hfe \leq 295$ and for the third transistors $40 \leq hfe < 70$ and for the fourth transistor $40 \leq hfe < 70$.

13 Claims, 2 Drawing Sheets

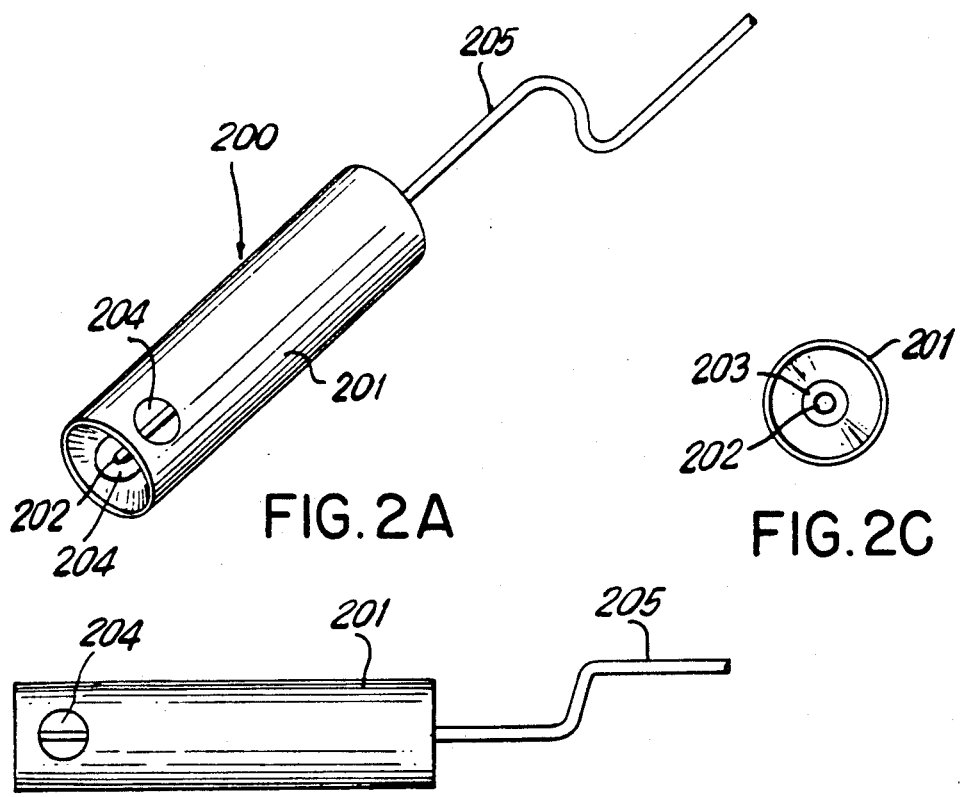
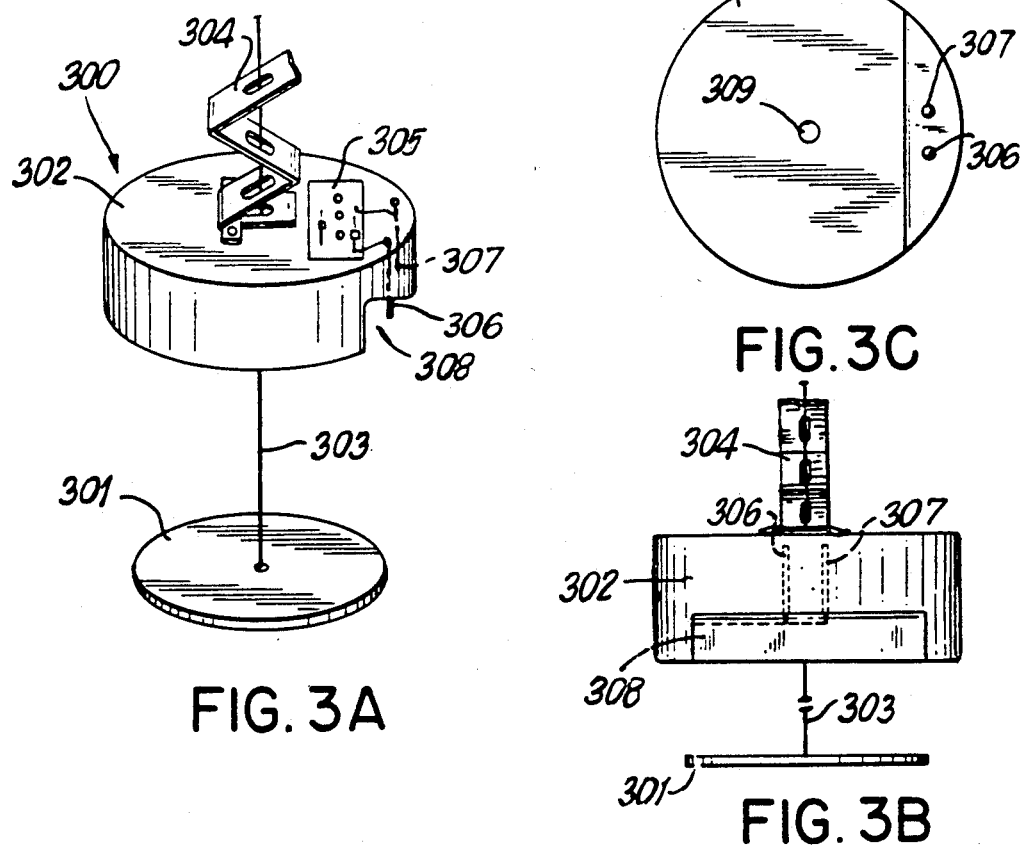

5,109,218

HYDROCARBON DETECTION CIRCUIT

BACKGROUND OF THE INVENTION

The present invention relates to a circuit for detecting hydrocarbons and which also has the ability to detect water and to indicate that neither hydrocarbons nor water are present.

It has become increasingly important to be able to detect the presence of hydrocarbons or to detect that a fluid which is present is not a hydrocarbon. This is particularly useful in leak detection systems wherein there is no ability to visually access the area surrounding an oil tank or a gas tank and therefore a detector must be capable of determining if a liquid in the vicinity of the gas tank or oil tank is only water or whether it is gas or oil leaking from the tank.

While there are presently a number of leak detectors, these detectors do not have the ability to directly determine whether a fluid is a hydrocarbon. Rather, these detectors indirectly determine that a fluid is a hydrocarbon by first determining whether or not a fluid is present and then whether or not the fluid is water.

SUMMARY OF THE INVENTION

The main object of the present invention is to provide a circuit which directly detects the presence of hydrocarbons.

Another object of the present invention is to provide a circuit for detecting hydrocarbons and water and for indicating when neither hydrocarbons nor water are present.

Still another object of the present invention is to provide a circuit for detecting hydrocarbons which is sufficiently sensitive but does not produce false readings.

These and other objects and advantages of the present invention are achieved in accordance with the present invention by a circuit for detecting hydrocarbons, comprising input means receptive of an input signal representative of electron movement in an unknown sample to be detected for producing a first amplified signal and signal processing means receptive of the first amplified signal from the input means for producing a first output signal when the input signal represents the presence of hydrocarbons, wherein the input means comprises four transistors connected as common base amplifiers with the base of a first of the four transistors receptive of the input signal, the base of a second of the four transistors connected to the emitter of the first transistor, the base of a third of the four transistors connected to the emitter of the second transistor, the base of a fourth of the four transistors connected to the emitter of the third transistor to produce the first amplified signal at the collector of the fourth transistor and wherein for the first transistor $70 < hfe \leq 120$, for the second transistor $150 < hfe \leq 295$, for the third transistor $40 < hfe < 70$ and for the fourth transistor $40 < hfe < 70$.

In a particularly advantageous preferred embodiment of the present invention, for the first transistor $hfe = 70$, for the second transistor $hfe = 178$, for the third transistor $hfe = 50$ and for the fourth transistor $hfe = 50$.

The input circuit preferably comprises four pnp transistors. The emitter of the first transistor is connected to the base of the second transistor with a first resistor therebetween, the emitter of the second transistor is connected to the base of the third transistor with a second resistor therebetween, the emitter of the third transistor is connected to the base of the fourth transistor with a third resistor therebetween and the base of the third transistor is connected to an emitter of the fourth transistor with a fourth resistor therebetween and wherein the collectors of the first, second and third transistors are connected together. Preferably, the first resistor has a resistance of $10M\Omega \pm 2\%$ the second resistor has a resistance of $6.8K\Omega \pm 2\%$, the third resistor has a resistance of $22K\Omega \pm 2\%$ and the fourth resistor has a resistance of $10M\Omega \pm 2\%$.

The circuit according to the present invention can be used to detect fluids with any conventional probe connected thereto with a two conductor, preferably coaxial, cable, with one conductor preferably connected to ground and a second conductor carrying the active signal.

In one embodiment, the circuit can be connected to a float sensor which has a base unit and a float which rises with a liquid level and which is connected with the detection circuit by means of a fan-fold cable. In accordance with the present invention, in order to reduce the false signals which are inherently generated by the movement of a fan-fold cable, the four transistors and four resistors of the input circuit are located in a printed circuit on the float and connected to the signal processing means by way of the fan-fold cable. In this way, the movement of the fan-fold cable does not generate false signals.

These and other features and advantages of the present invention will become more apparent from the following detailed description of the present invention, taken with the attached drawings, wherein:

BRIEF DESCRIPTION OF THE DRAWINGS

FIGS. 2A-2C are plan, side and front views of a probe according to the present invention; and FIGS. 3A-3C are plan, side and bottom views of a float type sensor according to the present invention.

DETAILED DESCRIPTION OF THE INVENTION

Figure 1:
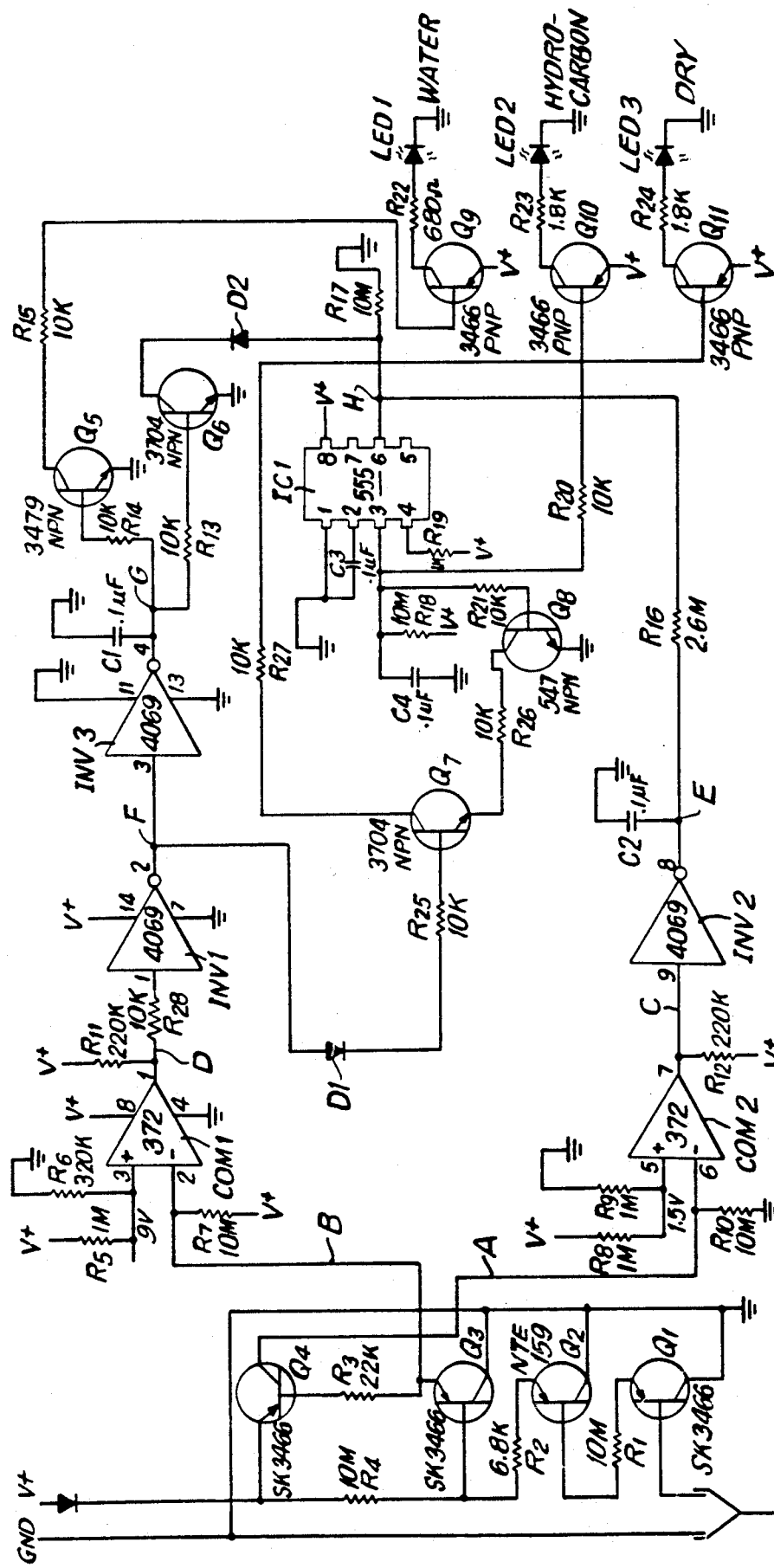
FIG. 1 is a schematic diagram of the detection circuit according to the present invention.

Referring now to FIG. 1, the circuit for detecting hydrocarbons and water includes input means comprising an input circuit having four transistors Q1-Q4 and resistors R1-R4. The input means receives an input signal by means of a coaxial connector connectable to a coaxial cable with the input signal being received at the base of transistor Q1 and the ground wire connected to the collectors of transistors Q1-Q3.

According to the theory of the present invention, while water is conductive and will provide a path between two electrodes on a probe and thus produce a current signal at the base of transistor Q1, hydrocarbons will not do so since they are non-conductive. Thus the circuit according to the present invention has the ability to sense electron movement caused by slight impurities in the hydrocarbons and this electron movement is sensed at the base of transistor Q1 and is amplified according to the amplification factor hfe of the transistor. This amplification is carried out in four stages in transistors Q1-Q4 so that the output A at the collector of transistor Q4 has sufficient current to generate a voltage than a reference voltage at the input to comparator as will be described hereinafter.

It is the combination of values of the amplification fact of transistors Q1-Q4 and the relationships between resistors R1-R4 which gives the input circuit according to the present invention the ability to detect the presence of hydrocarbons by this theory. According to the present invention, the amplification factor for the first transistor is $70 < hfe \leq 120$ and preferably 70, the amplification factor for the second transistor Q2 is $150 \leq hfe \leq 295$ and preferably 178, the amplification factor for the third transistor Q3 is $40 \leq hfe < 70$ and preferably 50 and the amplification factor for the fourth transistor Q4 is $40 \leq hfe < 70$ and preferably 50. The resistors R1-R4 are preferably $10M\Omega \pm 2\%$, $6.8K\Omega \pm 2\%$ and $10M\Omega \pm 2\%$ respectively.

The input circuit produces the first amplified signal A which indicates the presence of hydrocarbons and also produces a second amplified signal B which indicates the presence of water. Second amplified signal B is obtained at the emitter of transistor Q3. Since water is a relatively good conductor, the amplification needed for producing the current signal B is not as great as that needed for hydrocarbon and signal B is applied to the input of comparator COM1 across resistor R7 which compares the value thereof to a reference value produced by resistors R5 and R6 and which corresponds to 1.5 volts. COM2 compares the current signal A through resistor R10 to a reference value produced by resistors R8 and R9 which corresponds to 5 volts.

Normally, when no water or hydrocarbons are present, current signal A through resistor R10 is less than 5 volts and therefore the output C is high (approximately +V). Also the current signal B through resistor R7 is greater than 1.5 volts and therefore the output D of COM1 is low (approximately 0 volts). Upon the detection of hydrocarbons or water, signals C and D respectively reverse levels as determined by resistors R11 and R12. The signal D is applied through resistor R28 to inverter INV1 and is inverted to produce signal F. Signal C is applied to inverter INV2 and is inverted to produce signal E. Signal F is again inverted in inverter INV3 to produce signal G at its output. Signal F is applied to the base of transistor Q7 through resistor R25 and diode D1 and signal G is applied to the base of transistor Q5 through resistor R14 and the base of Q6 through resistor R13. The collector of transistor Q6 is connected through a diode D2 and across resistor R17 to the input H of timing circuit IC1 which is a CMOS 555 phase lock loop circuit. The output of inverter INV2 is also applied to the input H of IC1 via resistor R16 so that H is a combination of two input signals. The output I of IC1 is connected via resistor R21 to the base of transistor Q8 and is also connected via resistor R20 to the base of transistor Q10. The collector of transistor Q7 is connected by resistor R27 to the base of transistor Q11 and the collector of transistor Q5 is connected via resistor R15 to the base of transistor Q9. The emitter of transistor Q7 is connected to the collector of transistor Q8 by resistor R26. Transistors Q9, Q10 and Q11 control display light emitting diodes LED1, LED2 and LED3 through resistors R22, R23 and R24, respectively, in order to indicate the presence of water, hydrocarbon and dry, respectively, as will be explained later.

Capacitor C1 and C2 are provided for wave shaping and capacitors C3 and C4 and resistors R18 and R19 are provided for determining the timing of circuit IC1. As a result of the circuitry as shown, no output I is produced at terminal 3 unless the duration of the input H is greater than 6 seconds.

In the normal state when there is no liquid present, signal C is high and signal D is low, signal E is low and F is high and signal G is low. As a result, transistors Q5 and Q6 are off and transistor Q7 is on. Since the output E is low, signal H is low and thus the output I of IC1 is high. The fact that transistor Q5 is off means that transistor Q9 is off, the fact that signal I is high means that transistor Q10 is off and the fact that transistor Q7 is on means that transistor Q11 is conducting and thus LED3 is lit and indicating DRY.

When only water is present and sensed by conduction between electrodes on a conventional probe, the current signal B across R7 drops to less than 1.5 volts and the current signal A across R10 provides an input greater than 5 volts, causing output C to go low and output D to go high. This means that output E is high and F is low and output G is high. In this state, transistors Q5 and Q6 are both turned on and transistor Q7 is turned off. Signal H is therefore pulled to ground level and the output signal I remains high. The fact that transistor Q5 is on enables transistor Q9 to go on, whereas the fact that signal I is high turns off transistor Q10 and the fact that transistor Q7 is off turns off transistor Q11. Thus transistor Q9 enables the lighting of LED1 indicating WATER.

When hydrocarbons are present, the electron movement between two electrodes on a conventional probe is amplified and current signal A through R10 is sufficient to generate a voltage at the input of COM2 which is greater than 5 volts, and the input to COM1 is greater than 1.5 volts. In this situation, output C is low and output D is low and therefore signal E is high and signal F is high and signal G is low. As a result, transistor Q5 and Q6 are both off and transistor Q7 is on. Signal H is pulled high by signal E and signal I therefore goes low, thus turning transistor Q8 off. Transistor Q11 is turned off by the fact that transistor Q7 is on and transistor Q8 is off. The fact that transistor Q5 is off means that transistor Q9 will be off, the fact that signal I is low and Q8 is off enables transistor Q10 to be on and thus drive LED2 on indicating HYDROCARBON.

As noted earlier, this operation assumes the fact that signals A and B have a duration of at least 6 seconds. If the time of signals A and B is less than 6 seconds, output I will never go low and thus no reading will occur for hydrocarbon or water.

FIGS. 2A-2C show a probe for use with the detection circuit. The probe 200 includes a brass outer body 201 in a form of a cylinder and a stainless steel rod 202 in the center. Epoxy insulation 203 is disposed around the rod 202. The brass outer body 201 is connected to the braided shield of the coaxial cable 205 and the stainless steel rod 202 is connected to the center conductor of the shielded cable. The brass outer body 201 also includes apertures 204 approximately ⅜ inches in diameter when the probe is 2" in length and which permits the passage of fluids to the stainless steel rod 202.

FIGS. 3A-3C illustrate a float type sensor for determining liquid levels and for detecting hydrocarbons floating on top of water.

The float sensor 300 includes a round cable weight 301 which is 3" in diameter and about ¼" thick. Connected thereto is a stainless steel guide wire 303 which passes through a hole 309 in a float 302 which is about 2¼-⅞" thick and made of material in which it enables it to float on top of water or hydrocarbons.

A printed circuit 305 has the input circuit including transistors Q1-Q4 and resistors R1-R4 mounted on the top of the float 302 and a flex-fold or fan-fold cable 304 connects the signals A and D from the input circuit to the signal processing circuit. The electrodes 306 and 307 are stainless steel and spaced apart no more than $\frac{1}{4}''$ and extend downwardly from the float in a cutaway portion 308 approximately $\frac{1}{4}''$ so that only a $\frac{1}{4}''$ is exposed to the liquid.

What is claimed is:

1. A circuit for detecting hydrocarbons, comprising: input means receptive of a signal representative of electron movement in an unknown sample to be detected for producing a first amplified signal; and signal processing means receptive of the first amplified signal form the input means for producing a first output signal when the input signal represents the presence of hydrocarbons, wherein the input means comprises four transistors connected as common base amplifiers with the base of a first of the four transistors receptive of the input signal, the base of a second of the four transistors connected to the emitter of the first transistor, the base of a third of the four transistors connected to the emitter of the second transistor, the base of a fourth of the four transistors connected to the emitter of the third transistor to produce the first amplified signal at the collector of the fourth transistor and wherein for the first transistor $70 < hfe \leq 120$, for the second transistor $150 \leq hfe \leq 295$, for the third transistor $40 \leq hfe < 70$ and for the fourth transistor $40 \leq hfe < 70$.

2. The circuit according to claim 1, wherein for the first transistor $hfe = 70$, for the second transistor $hfe = 178$, for the third transistor $HFE = 50$ and the fourth transistor $hfe = 50$.

3. The circuit according to claim 2, wherein the four transistors are pnp transistors.

4. The circuit according to claim 3, wherein the emitter of the first transistor is connected to the base of the second transistor with a first resistor therebetween, the emitter of the second transistor is connected to the base of the third transistor with a second resistor therebetween, the emitter of the third transistor is connected to the base of the fourth transistor with a third resistor therebetween and the base of the third transistor is connected to an emitter of the fourth transistor with a fourth resistor therebetween and wherein collectors of the first, second and third transistor are connected together.

5. The circuit according to claim 4, wherein the first resistor has a resistance of $10M\Omega \pm 2\%$, the second resistor has a resistance of $6.8K\Omega \pm 2\%$, the third resistor has a resistance of $22K\Omega \pm 2\%$ and the fourth resistor has a resistance of $10M\Omega \pm 2\%$.

6. The circuit according to claim 1, wherein the signal processing means comprises first means for comparing the first amplified signal to a first reference value.

7. The circuit according to claim 1, wherein the signal processing means has means for detecting water comprising second means for comparing a second amplified signal produced at the emitter of the third transistor to a second reference value and for producing a second output signal when the second amplified signal is representative of water.

8. The circuit according to claim 7, wherein the signal processing means further comprises means for producing a third output signal when the first and second amplified signals do not correspond to the presence of hydrocarbons or water.

9. The circuit according to claim 7, wherein the signal processing means comprises means for preventing the production of the first and second output signals when the first and second amplified signals have a duration below a given time value to prevent a false indication.

10. The circuit according to claim 1, further comprising means for producing the input signal comprising sensor means and a cable connecting the sensor means to the input means.

11. The circuit according to claim 10, wherein the sensor means comprises a float and electrodes fixed to the float.

12. The circuit according to claim 11, wherein the four transistors are mounted on the float and the first amplified signal is connected to the signal processing means by a fan-fold cable.

13. The circuit according to claim 6, wherein the sensor means comprises a probe having two electrodes including a metal outer body and a metal rod disposed concentrically within the outer body with insulation therebetween.

* * * * *